(12) United States Patent
Xie et al.

(10) Patent No.: US 11,714,073 B2
(45) Date of Patent: *Aug. 1, 2023

(54) PHOTOIONIZATION DETECTOR AUTOMATED ZERO LEVEL CALIBRATION

(71) Applicant: Honeywell International Inc., Charlotte, NC (US)

(72) Inventors: Guangli Xie, Shanghai (CN); Bo Chen, Shanghai (CN); Zhanghua Wu, Shanghai (CN); Yaofu Gong, Kunshan (CN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/820,608

(22) Filed: Aug. 18, 2022

(65) Prior Publication Data

US 2022/0390424 A1 Dec. 8, 2022

Related U.S. Application Data

(63) Continuation of application No. 17/176,542, filed on Feb. 16, 2021, now Pat. No. 11,480,554, which is a
(Continued)

(51) Int. Cl.
*G01N 27/66* (2006.01)
*G01N 30/64* (2006.01)
(Continued)

(52) U.S. Cl.
CPC ......... *G01N 33/0006* (2013.01); *G01N 27/66* (2013.01); *G01N 30/64* (2013.01);
(Continued)

(58) Field of Classification Search
CPC .... G01N 33/0006; G01N 27/66; G01N 30/64; G01N 33/0047; G01N 30/8665; G01N 2030/642
See application file for complete search history.

(56) References Cited

U.S. PATENT DOCUMENTS 2,901,625 A 8/1959 Herbert et al.
5,393,979 A 2/1995 Hsi
(Continued)

FOREIGN PATENT DOCUMENTS

CN 102072945 A 5/2011
CN 103424465 A 12/2013
(Continued)

OTHER PUBLICATIONS

AU Office Action dated Nov. 13, 2020 for AU Application No. 2020201513, 7 pages.
(Continued)

*Primary Examiner* — David P Porta
*Assistant Examiner* — Fani Polyzos Boosalis
(74) *Attorney, Agent, or Firm* — Alston & Bird LLP

(57) ABSTRACT

A method of detecting gas includes determining and storing, by a controller, a zero level of a photoionization detector using ambient air inflow when an ultraviolet lamp is in a turned OFF state, wherein the stored zero level is based on an ambient temperature; sampling, by the controller, an output of a detector electrode of the photoionization detector when the ultraviolet lamp is in a turned ON state; and comparing the sampled output of the detector electrode to the stored zero level to determine if a threshold concentration of a gas is present.

17 Claims, 6 Drawing Sheets

Related U.S. Application Data continuation of application No. 16/988,180, filed on Aug. 7, 2020, now Pat. No. 10,969,371, which is a continuation of application No. 16/090,391, filed as application No. PCT/US2016/044614 on Jul. 29, 2016, now Pat. No. 10,782,273.

(51) Int. Cl.
  *G01N 33/00* (2006.01)
  *G01N 30/86* (2006.01)

(52) U.S. Cl.
  CPC ..... *G01N 33/0047* (2013.01); *G01N 30/8665* (2013.01); *G01N 2030/642* (2013.01)

(56) References Cited

U.S. PATENT DOCUMENTS

| | | |
|---|---|---|
| 5,701,009 A | 12/1997 | Griffiths et al. |
| 5,773,833 A | 6/1998 | Hsi |
| 6,225,633 B1 | 5/2001 | Sun et al. |
| 6,313,638 B1 | 11/2001 | Sun et al. |
| 6,967,485 B1 | 11/2005 | Hsueh et al. |
| 8,362,445 B2 | 1/2013 | Short et al. |
| 9,459,235 B2 | 10/2016 | Soundarrajan et al. |
| 9,645,112 B2 | 5/2017 | Chan |
| 10,782,273 B2 | 9/2020 | Xie et al. |
| 10,969,371 B2 | 4/2021 | Xie et al. |
| 11,162,917 B2 | 11/2021 | Liu et al. |
| 2008/0220535 A1 | 9/2008 | Leboeuf et al. |
| 2012/0089019 A1 | 4/2012 | Fan |
| 2012/0252347 A1 | 10/2012 | Chan |
| 2012/0279277 A1 | 11/2012 | Parusel et al. |
| 2021/0181170 A1 | 6/2021 | Xie et al. |
| 2022/0011266 A1 | 1/2022 | Liu et al. |

FOREIGN PATENT DOCUMENTS

| | | |
|---|---|---|
| CN | 205027697 U | 2/2016 |
| CN | 10365693 | 4/2020 |
| DE | 102011114943 A1 | 4/2012 |
| EP | 1262770 A2 | 12/2002 |
| EP | 2458375 A1 | 5/2012 |
| WO | 94/27141 A1 | 11/1994 |
| WO | 2011/090433 A1 | 7/2011 |
| WO | 2018/022072 A1 | 2/2018 |

OTHER PUBLICATIONS

CA Notice of Allowance dated Mar. 28, 2022 for CA Application No. 3074213, 1 page.
CN Notice of Allowance dated Jan. 19, 2022 for CN Application No. 201680085323, 1 page.
Communication about intention to grant a European patent dated Apr. 22, 2021 for EP Application No. 16753755.4, 5 pages.
Communication pursuant to Article 94(3) for European Application No. 16753755.4, dated Mar. 12, 2020, 4 pages.
Communication pursuant to Rules 161(1) and 162 for European Patent Application No. 16753755.4 dated Oct. 24, 2018, 3 pages.
Communication pursuant to Rules 70(2) and 70a(2) for European Patent Application No. 20160284.4 dated Sep. 7, 2020, 2 pages.
Corrected Notice of Allowability dated Jun. 29, 2020 for U.S. Appl. No. 16/090,391.
Decision to grant a European patent received for European Application No. 16753755.4, dated Aug. 5, 2021, 2 pages.
English translation of CN Notice of Allowance dated Jan. 19, 2022 for CN Application No. 201680085323, 2 pages.
Examination Report No. 2 issued in Australian Application No. 2020201513 dated Apr. 1, 2021, 5 pages.
Extended European Search Report for Patent Application No. 20160284.4 dated Jul. 17, 2020, 11 pages.
Extended European Search Report issued in European Application No. 21153809.5 dated Apr. 26, 2021, 9 pages.
Intention to grant issued in European Application No. 16753755.4 dated Nov. 11, 2020, 5 pages.
International Search Report and Written Opinion for corresponding International Application No. PCT/US2016/044614, dated Jan. 12, 2016, 14 pages.
Jun et al. "Technology and Evaluation of Foreign Chemical Poison Detector," National Defense Industry Press, p. 322, 326.
Non-Final Office Action received for U.S. Appl. No. 17/176,542, dated Nov. 16, 2021, 5 pages.
Non-Final Rejection dated Apr. 12, 2021 for U.S. Appl. No. 16/804,066.
Non-Final Rejection dated Feb. 25, 2020 for U.S. Appl. No. 16/090,391.
Non-Final Rejection dated Nov. 16, 2021 for U.S. Appl. No. 17/176,542.
Non-Final Rejection dated Sep. 14, 2022 for U.S. Appl. No. 17/483,157.
Non-Final Rejection dated Sep. 17, 2020 for U.S. Appl. No. 16/988,180.
Notice of Acceptance issued in Australian Application No. 2020201513 dated Aug. 5, 2021, 3 pages.
Notice of Allowance and Fees Due (PTOL-85) dated Apr. 21, 2022 for U.S. Appl. No. 17/176,542.
Notice of Allowance and Fees Due (PTOL-85) dated Dec. 2, 2020 for U.S. Appl. No. 16/988,180.
Notice of Allowance and Fees Due (PTOL-85) dated Dec. 18, 2020 for U.S. Appl. No. 16/988,180.
Notice of Allowance and Fees Due (PTOL-85) dated Jan. 26, 2021 for U.S. Appl. No. 16/988,180.
Notice of Allowance and Fees Due (PTOL-85) dated Jun. 29, 2020 for U.S. Appl. No. 16/090,391.
Notice of Allowance and Fees Due (PTOL-85) dated Mar. 2, 2022 for U.S. Appl. No. 17/176,542.
Notice of Allowance and Fees Due (PTOL-85) dated May 11, 2020 for U.S. Appl. No. 16/090,391.
Notice of Allowance and Fees Due (PTOL-85) dated May 27, 2022 for U.S. Appl. No. 17/176,542.
Notice of Allowance received for U.S. Appl. No. 16/804,066, dated Jun. 25, 2021, 9 pages.
Notice of Allowance received for U.S. Appl. No. 16/804,066, dated Oct. 6, 2021, 6 pages.
Notice of Allowance received for U.S. Appl. No. 17/176,542, dated Apr. 21, 2022, 2 pages.
Notice of Allowance received for U.S. Appl. No. 17/176,542, dated Mar. 2, 2022, 10 pages.
Notice of Allowance received for U.S. Appl. No. 17/176,542, dated May 27, 2022, 7 pages.
Notice of Grant of Patent Right for Chinese Application No. 201920254732.1, dated Jan. 17, 2020, 6 pages.
Office Action for Chinese Application No. 201920254732.1, dated Oct. 22, 2019, 3 pages.
Office Action issued in Canadian Application No. 3,074,213 dated Apr. 30, 2021, 4 pages.
Office Action issued in Chinese Application No. 201680085323.2 dated Jul. 2, 2021, 24 pages.
Office Action issued in Chinese Application No. 201680085323.2 dated Nov. 27, 2020, 24 pages.
Office Action received for European Application No. 20160284.4, dated Sep. 2, 2022, 5 pages.
Photoionization Detectors, Chapter 6, https://web.archive.org/web/20050119175603/http://intlsensor.com/pdf/photoionization.pdf, Retrieved Dec. 5, 2018, 9 pages, Jan. 16, 2005, 9.
U.S. Appl. No. 17/176,542, filed Feb. 16, 2021, 2021-0181170 A1, Patented.
U.S. Appl. No. 16/988,180, filed Aug. 7, 2020, U.S. Pat. No. 10,969,371, Patented.
U.S. Appl. No. 16/090,391, filed Oct. 1, 2018, U.S. Pat. No. 10,782,273, Patented.
AU Office Action dated Nov. 2, 2022 for AU Application No. 2021269436.

(56) References Cited

OTHER PUBLICATIONS

Notice of Allowance and Fees Due (PTOL-85) dated Nov. 9, 2022 for U.S. Appl. No. 17/483,157.

PHOTOIONIZATION DETECTOR AUTOMATED ZERO LEVEL CALIBRATION

CROSS-REFERENCE TO RELATED APPLICATIONS

This application is a continuation of U.S. patent application Ser. No. 17/176,542 filed on Feb. 16, 2021, which is a continuation of U.S. patent application Ser. No. 16/988,180 filed on Aug. 7, 2020, now U.S. Pat. No. 10,969,371, which is a continuation of Ser. No. 16/090,391 filed on Oct. 1, 2018, now U.S. Pat. No. 10,782,273, which is a national phase entry of International Application No. PCT/US2016/044614, filed Jul. 29, 2016, each of which is incorporated herein by reference in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Photoionization detectors (PIDs) employ a lamp to emit photons that ionize gases in the proximity of detector electrodes. An electric field is established between the plates of the electrodes by an applied voltage bias. The electric field induces ionized particles to move to one or another plate, thereby establishing an electric current between the electrodes. The electric current can be processed to extract indication of the presence of gas. For example, PIDs may be used to detect the presence and/or concentration of volatile organic compounds (VOCs) which can pose a threat to human beings.

SUMMARY

In an embodiment, a method of detecting gas with a photoionization detector (PID) system is disclosed. The method comprises powering on a photoionization detector, turning off an ultraviolet lamp of the photoionization detector by a controller of the photoionization detector system and keeping it turned off during the zero calibration procedure, flowing ambient air from a surrounding environment by a fan of the photoionization detector system past a detector electrode of the photoionization detector, processing an output of the detector electrode by the controller to determine a zero level of the photoionization detector, and storing the zero level by the controller in a memory of the photoionization detector system, wherein the photoionization detector in a detecting mode compares an output of the detector electrode to the zero level to determine if a threshold concentration of a gas is present.

In another embodiment, a photoionization detector (PID) system is disclosed. The photoionization detector comprises a detector electrode that outputs a signal, an ultraviolet lamp, a lamp driver communicatively coupled to the ultraviolet lamp and configured to turn the ultraviolet lamp on and off in response to a control input, a controller that is communicatively coupled to the output signal of the detector electrode and to the control input of the lamp driver, that outputs an indication of gas detection based on the output signal of the detector electrode and based on a zero calibration level stored in the photoionization detector system, and a zero calibration application stored in a memory of the photoionization detector system. When executed by the controller, the zero calibration application turns off an ultraviolet lamp of the photoionization detector system during a zero calibration procedure, processes the output signal of the detector electrode, while ambient air from the surrounding environment flows past the detector electrode, to determine a zero level of the photoionization detector system, and stores the zero level in the photoionization detector system.

In yet another embodiment, a method of detecting presence of a gas by a photoionization detector (PID) system is disclosed. The method comprises powering on a photoionization detector, turning off an ultraviolet lamp of the photoionization detector by a controller of the photoionization detector system during the zero calibration procedure, flowing ambient air from a surrounding environment by a fan of the photoionization detector system past a detector electrode of the photoionization detector, processing an output of the detector electrode by the controller to determine a zero level of the photoionization detector, and storing the zero level by the controller in a memory of the photoionization detector system, wherein the photoionization detector system in a detecting mode compares an output of the detector electrode to the zero level to determine if a threshold concentration of a gas is present. The method further comprises, after the zero level is stored, turning the ultraviolet lamp on and off periodically by the controller, after the zero level is stored, analyzing by the controller the sampling of the output of the detector electrode, determining by the controller a concentration of gas based on the stored zero level and based on the analyzing of the output of the detector electrode after the zero level is stored, and outputting a gas detection indication by the controller based on the determination of the concentration of gas.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
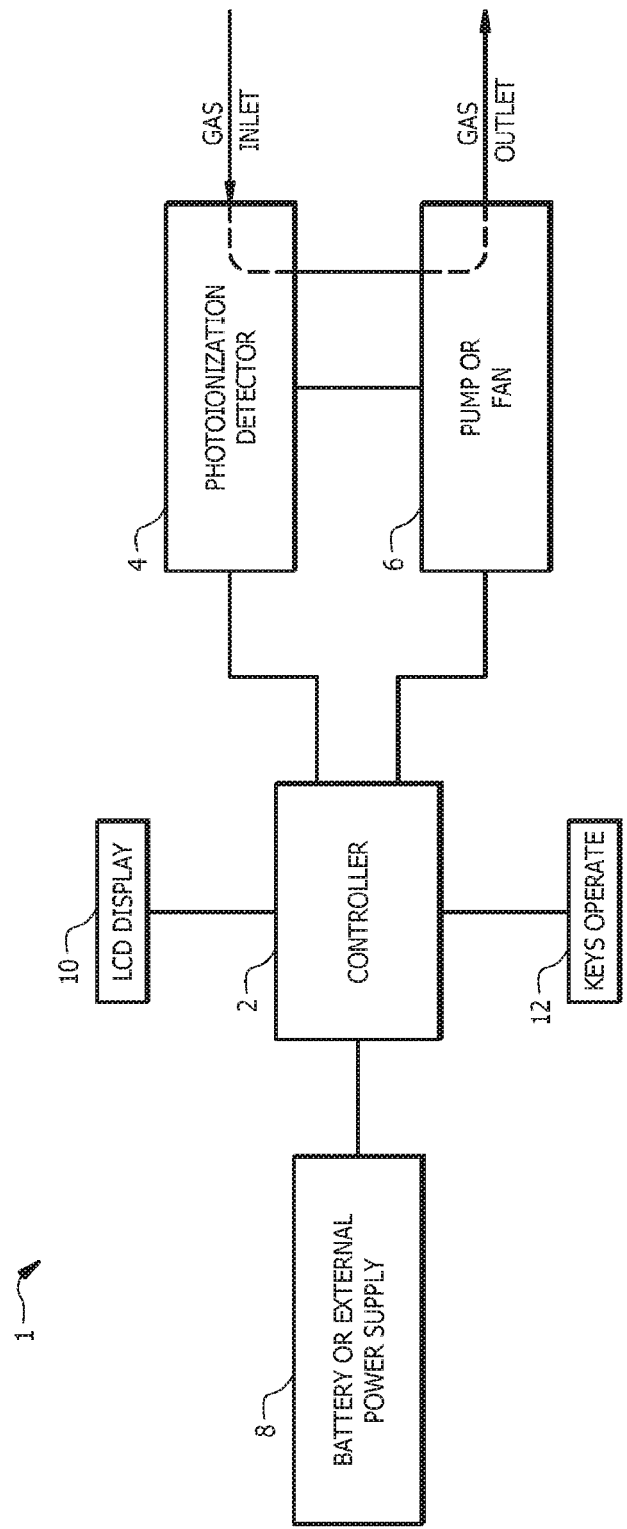
FIG. 1 is a block diagram of a photoionization detector system according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The present disclosure teaches a photoionization detector (PID) that performs zero level calibration without using specialized gas but instead simply uses the ambient air, whatever gases it may contain at the time. This is in contrast to known methods that entail providing a special source of calibration gas such as nitrogen. Providing calibration gas can be expensive and complicates the process of calibrating the HD. The PID disclosed herein may be provided in the form factor of a handheld device that may be carried by a worker in a potentially hazardous work environment where dangerous gases such as benzene, toluene, gasoline, fuel oil, diesel fuel, or other volatile organic compounds (VOCs) may present a hazard to a worker. These environments, without limitation, may include oil refineries, chemical plants, manufacturing plants, and others. In some cases, the PID of the present disclosure may be mounted separately from human beings in portions of an infrastructure and may be communicatively coupled to a monitoring system.

The principle of operation of a PID is to radiate ultraviolet light onto a flow of gas from an environment proximate to a pair of electrically biased electrodes. If VOCs are present, the ultraviolet gas ionizes some of the VOC gas, the ions are collected at one or the other electrode producing an electric current that may be amplified and filtered and analyzed to determine a magnitude of electric current which represents the concentration of VOCs. The greater the current, the greater the concentration of VOCs. A zero level may be determined during calibration and stored in the processor or memory of the PID. When detecting concentration of VOCs, the electric current level is compared to the zero level that was stored to determine the concentration of gas.

The prior art method of performing zero calibration entails providing a gas which does not ionize in response to radiation with ultraviolet light and hence provides no incremental electric current in the electrodes. The current disclosure teaches turning off the ultraviolet lamp while performing the zero calibration. When this is done, there is substantially no incremental electric current due to ionization in the electrodes. Even if there may be VOCs present, since the ultraviolet lamp is turned off, the VOCs are not ionized and there is little or no incremental electric current. This provides the condition desired to determine an electric current level that is present when no ions are present. This process can be analogized to determining a tare weight for measuring a weight in a container—the weight of the container is subtracted from the combined weight of the container and the contents of the container to determine the weight of the contents alone.

Turning now to FIG. 1, a photoionization detector (PID) system 1 is described. In an embodiment, the MD system 1 comprises a controller 2, a photoionization detector 4, a fan 6, a battery 8 or external power supply, a visual display 10, and an input device 12. The photoionization detector system 1 may be similar in some aspects to the PID system 100 described below with reference to FIG. 4, FIG. 5, FIG. 6, and FIG. 7. Here the emphasis is on the zero level calibration aspects of the MD system 1; below the emphasis is on the components of the PID system 100 and their function after the zero level has been determined.

Gas from the ambient environment is drawn in past the photoionization detector 4 by the fan 6. During zero calibration, the ultraviolet lamp in the photoionization detector 4 is turned off and hence any gas, for example any VOCs, present in inflowing air is not ionized because there is no ultraviolet light radiation to ionize the gas molecules. The electrical output of the photoionization detector 4 is measured or sampled by the controller 2 during this zero calibration process (i.e., while the ultraviolet lamp is turned off), and the zero level is stored in the controller 2 and/or a memory communicatively coupled to the controller 2. In an embodiment, the zero level may be a count associated with the zero level. In an embodiment, the zero level may be a digital value output by an analog-to-digital converter of the photoionization detector 4. The PID system 1 may be powered by the battery 8 or by an external power supply (i.e., in the case that the PID system 1 is not a handheld device but is coupled to an infrastructure in a refinery or manufacturing plant). The visual display 10 may provide visual feedback that the zero calibration process has been started and when the zero calibration process has completed.

The zero level may be determined by maintaining the ultraviolet light in the photoionization detector 4 may be held off through the entire time duration of the zero level determination process. Alternatively, in an embodiment, the ultraviolet light may be turned off and on with a predefined on duty cycle, and the electrical output of the photoionization detector 4 is captured while the ultraviolet light is turned off, for example after the ultraviolet light has been turned off long enough for deionization to have substantially completed. The captured output of the photoionization detector 4 is then used to determine the zero level.

A worker may use the input device 12, for example a keypad or other input device, to initiate the zero calibration process at the start of a work day, at the start of a work week, or on some other schedule. The visual display 10 may also provide alerts to the presence of hazardous gas, for example the presence of VOCs. The visual display 10 may provide an indication of the concentration of gas, for example quantified in parts per billion (ppb) or in parts per million (ppm). The visual display 10 and/or an aural alert (not shown) may provide an attention getting alert when the concentration of gas exceeds a predefined concentration threshold. For example, a red indication may flash on the visual display 10 and/or an alarm may sound. In an embodiment, the PID system 1 may further comprise a vibrator (not shown) that may vibrate to convey an alert to the worker in a high-noise work environment where an aural alert may be missed by a worker.

The zero calibration process may be performed over a time duration of about 1 minute, over a time duration of about 5 minutes, over a time duration of about 15 minutes, over a time duration of about 1 hour, over a time duration of about 4 hours, over a time duration of about 12 hours, over a time duration of about 24 hours, or over a time duration that is intermediate between any two of these time durations.

The determination of the gas concentration by the controller 2 can be performed in a manner such as the following:

$$\text{Gas Concentration} = \text{Sensitivity} \times (\text{Count}_{gas} - \text{Count}_{zero}) \quad \text{EQ 1}$$

Where $\text{Count}_{zero}$ is the stored zero level, and where $\text{Count}_{gas}$ is the value of the level or count of sensed gas sensed by the photoionization detector during gas sensing. As discussed further below, $\text{Count}_{gas}$ may be the value of the level or count of sensed gas determined shortly after the ultraviolet lamp has been turned off. As discussed further below, the ultraviolet lamp may be turned off and on periodically rather than left on continuously to conserve and extend battery power. For example, the on duty cycle of the ultraviolet lamp may be less than 10%. For example, the on duty cycle of the ultraviolet lamp may be less than 2%. The reduced on duty cycle of the ultraviolet lamp can also extend the life of the ultraviolet lamp and slow the rate of deposit of polymer deposition on the ultraviolet lamp and/or lamp window. In an embodiment, the ultraviolet lamp may be a vacuum ultraviolet (VUV) lamp.

By performing the zeroing procedure, the effect of ambient temperature changes can be readily adapted to by the PID system 1. For example, a worker may initiate a zeroing procedure for the PH) system 1 when moving from a first work area having a first ambient temperature to a second work area having a second ambient temperature. Alternatively, the HD system 1 may sense external temperature and adapt the zero level of value $Count_{zero}$ algorithmically based on sensed external temperature accordingly.

Figure 2:
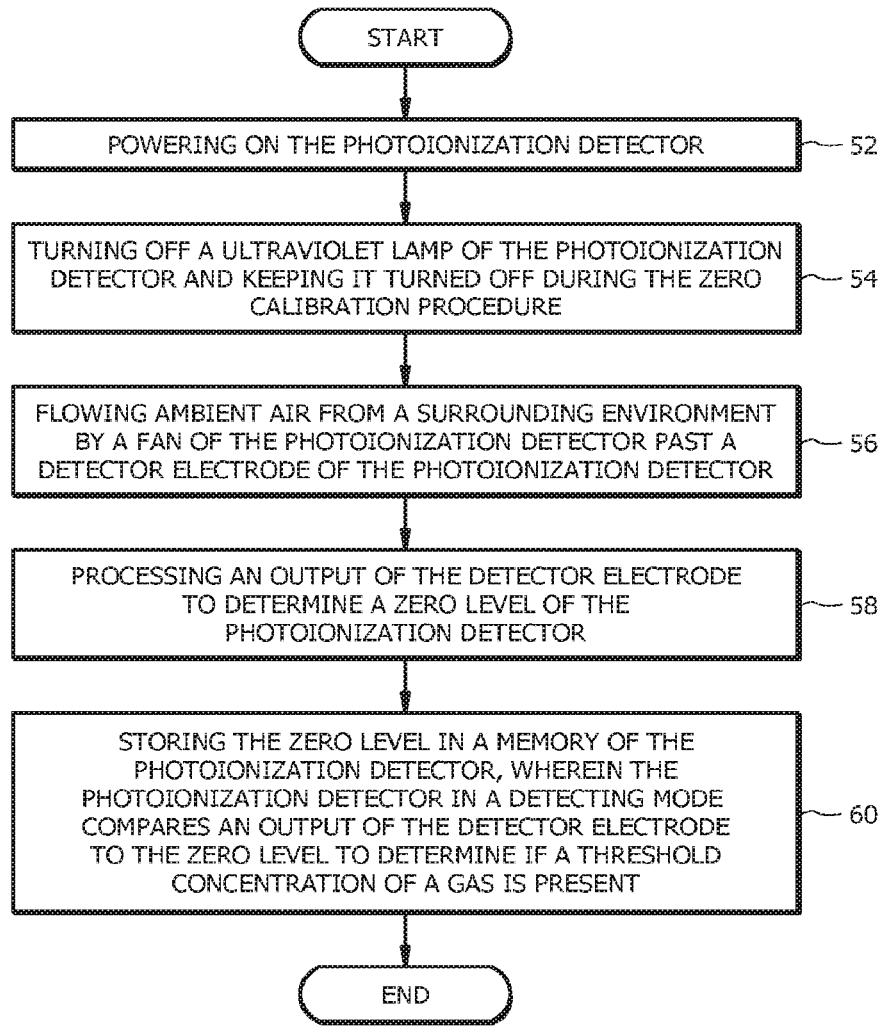
FIG. 2 is a flow chart of a method according to an embodiment of the disclosure.

Turning now to FIG. 2 a method 50 for detecting a gas with the photoionization detector system 1 is described. At block 52, a photoionization detector is powered on. At block 54, an ultraviolet lamp of the photoionization detector is turned off and kept turned off during the zero calibration procedure. Alternatively, the photoionization detector is turned off and on alternatively, with the on duty cycle being less than 50%, less than 10%, or less than 2% of the period of the on-off periodic cycle. At block 56, ambient air is flowed from a surrounding environment by a fan of the photoionization detector past a detector electrode of the photoionization detector. At block 58, an output of the detector electrode is processed to determine a zero level of the photoionization detector. The output of the detector electrode is sampled at a time when the ultraviolet light is turned off, for example a predefined duration of time after the ultraviolet light is turned off to allow most ionized gas molecules to deionize. At block 60, the zero level is stored in a memory of the photoionization detector system 1, wherein the photoionization detector system 1 in a detecting mode compares an output of the detector electrode to the zero level to determine if a threshold concentration of a gas is present. In an embodiment, the process of method 50 is performed each time the photoionization detector system 1 is powered on. In an embodiment, the process of method 50 may further be initiated and performed in response to a user input using the input device 12, for example on the occasion of the user moving from a first work environment to a second work environment (e.g., from an indoor work environment to an outdoor work environment.

Figure 3:
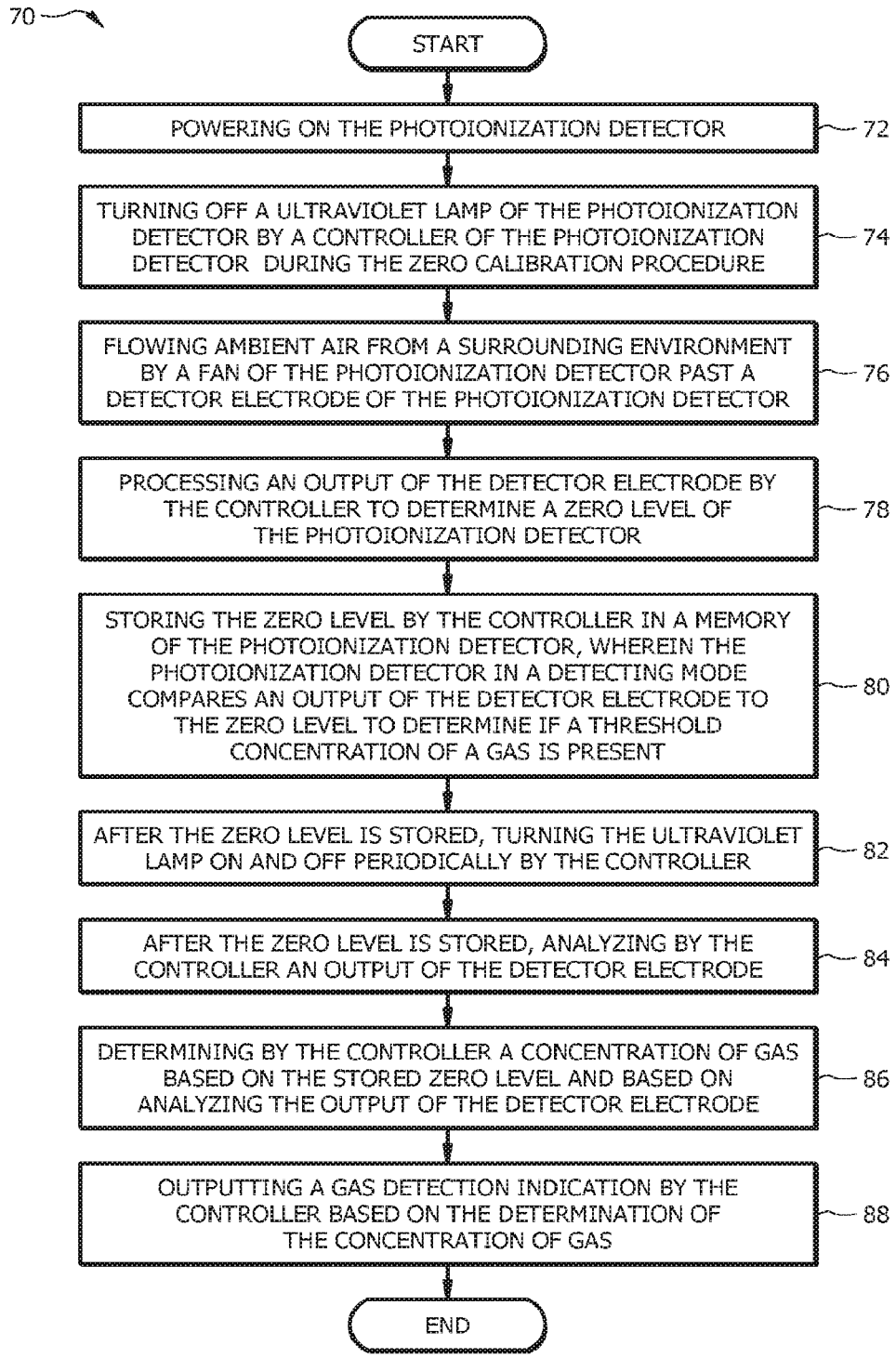
FIG. 3 is a flow chart of another method according to an embodiment of the disclosure.

Turning now to FIG. 3, a method 70 for detecting presence of a gas by a photoionization detector system 1 is described. At block 72, a photoionization detector is powered on. At block 74, an ultraviolet lamp of the photoionization detector is turned off by a controller of the photoionization detector system 1 and keeping it turned off during the zero calibration procedure. Alternatively, the photoionization detector is turned off and on alternatively, with the on duty cycle being less than 50%, less than 10%, or less than 2% of the period of the on-off periodic cycle. At block 76, ambient air from a surrounding environment is flowed by a fan of the photoionization detector system 1 past a detector electrode of the photoionization detector. At block 78, an output of the detector electrode is processed by the controller to determine a zero level of the photoionization detector. The output of the detector electrode is sampled at a time when the ultraviolet light is turned off, for example a predefined duration of time after the ultraviolet light is turned off to allow most ionized gas molecules to deionize.

At block 80, the zero level is stored by the controller in a memory of the photoionization detector system 1, wherein the photoionization detector system 1 in a detecting mode compares an output of the detector electrode to the zero level to determine if a threshold concentration of a gas is present. At block 82, after the zero level is stored, the ultraviolet lamp is turned on and off periodically by the controller. In an embodiment, the photoionization detector is turned off and on alternatively, with the on duty cycle being less than 50%, less than 10%, or less than 2% of the period of the on-off periodic cycle. At block 84, after the zero level is stored, the controller analyzes an output of the detector electrode. At block 86, the controller determines a concentration of gas based on the stored zero level and based on the analyzing of the output of the detector electrode after the zero level is stored. At block 88, the controller outputs a gas detection indication based on the determination of the concentration of gas. For example, the visual display 10 may indicate a concentration of gas in parts per billion (ppb) or in parts per million (ppm). Alternatively, the photoionization detector system 1 may present an alarm such as by visual alert on the visual display 10, an aural alert, and/or a vibration alert, if the concentration of gas exceeds a predefined alerting threshold.

In an embodiment, a lamp driver is turned on and off by a controller, turning on and off the MD lamp. The PID lamp is turned on for a relatively short duty time, for example less than 10% of the time. This reduces the power load on the battery. Additionally, this extends the life of the PID lamp and reduces the rate of polymer deposition on the PID lamp and/or PID lamp window. A signal conditioning circuit that receives the output of a HD sensor and/or PID electrodes is turned off and on by the controller, enabling signal sampling, conditioning, and outputting of signal to the controller for determining an indication of presence or absence of gas. The controller turns the signal conditioning circuit on only after the PID lamp driver (and hence the PID lamp) is turned off. Because the PID lamp driver and/or PID lamp, when turned on, create electric noise in the PID, sampling and signal conditioning when the HD lamp driver and PID lamp are turned off reduces the noise that enters the signal conditioning circuit. Because there is less electric noise, the filtering time constant of the signal conditioning circuit can be substantially reduced, thereby increasing the response time of the PID.

Figure 4:
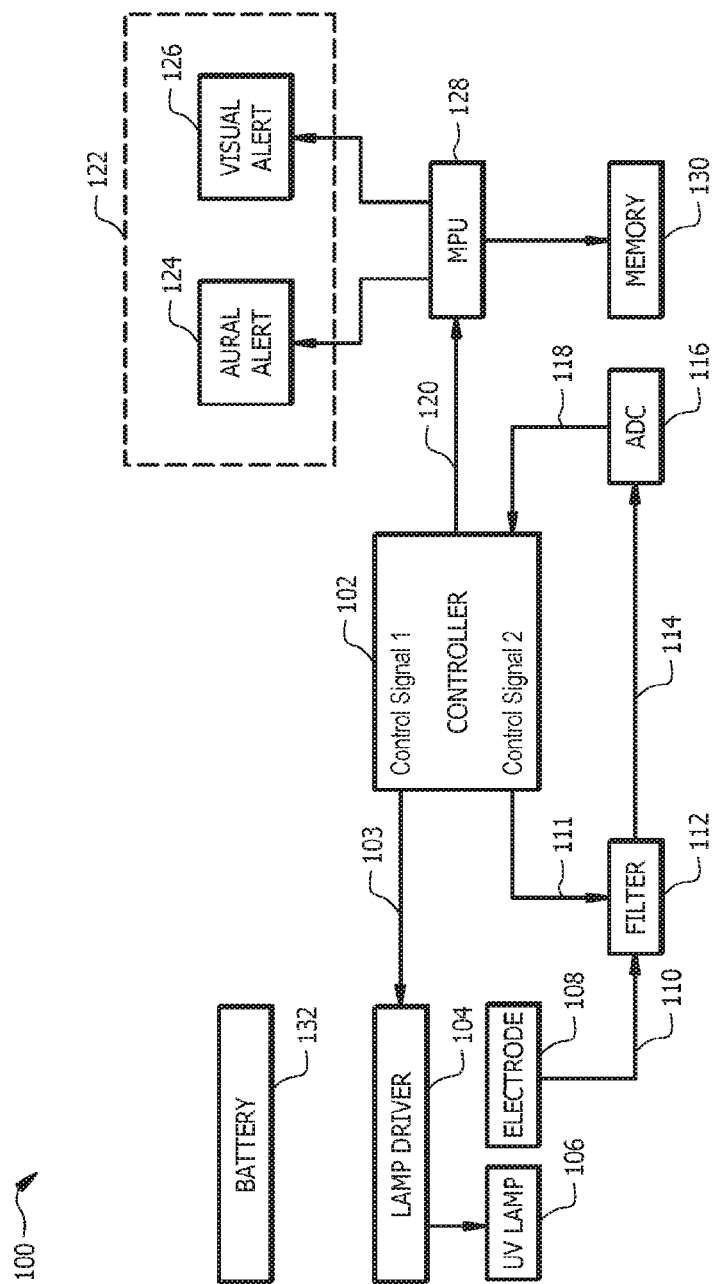
FIG. 4 is a block diagram of a system according to an embodiment of the disclosure.

Turning now to FIG. 4, a PID system 100 is described. In an embodiment, this MD system 100 may be substantially similar to the HD system 1 described above with reference to FIG. 1, FIG. 2, and FIG. 3. In an embodiment, the PID system 100 comprises a controller 102, a lamp driver 104, an ultraviolet (UV) lamp 106, an electrode 108, a filter 112, and an analog-to-digital converter 116. The controller 102 may be a microcontroller, an application specific integrated circuit (ASIC), a programmable logic device (PLD), a field programmable gate array (FPGA), or some other logic processor. The lamp driver 104 is configured to provide power and/or stimulate the UV lamp 106 to emit UV light. In an embodiment, the UV lamp 106 may be associated with a window (not shown) through which UV light emitted by the UV lamp 106 passes before radiating the vicinity of the electrode 108. The electrode 108 may comprise at least two parallel plates of electrodes that are provided a stable direct current (DC) bias voltage.

When the UV lamp 106 is turned on, UV light emitted by the UV lamp 106 ionizes gases, if present, in the vicinity of the electrode 108, and an electric field between the plates of the electrode 108 induces a current flow that is proportional to the presence of ionized gas molecules. Note that when the UV lamp 106 is turned off, the process of ionization stops but the already ionized gas molecules do not immediately deionize, hence a current flow may continue between the plates of the electrode 108 for some time after the UV lamp 106 is turned off, if there are gases present (e.g., if volatile organic compounds (VOCs) are present). When the UV lamp 106 is turned on, electric noise is induced into the PID by the UV lamp 106 and/or the lamp driver 104. When the UV lamp 106 and lamp driver 104 are turned off by the controller 102, this source of electric noise is eliminated.

The controller 102 turns the lamp driver 104 on and off via a first control signal 103. In an embodiment, the controller 102 turns the lamp driver 104 on and off periodically and with an on duty cycle of less than 10%. As is understood by one skilled in the art, a duty cycle is a representation of the amount of time something is turned on versus turned off, often represented as a percentage. As an example, if the period is 1 second (S), a 10% on duty cycle would turn the lamp driver 104 on for about 100 milliseconds (mS) and off for about 900 mS in every 1 S period. In another example, if the period is 1 second, a 1% on duty cycle would turn the lamp driver 104 on for about 10 mS and off for about 990 mS in every 1 S period. As another example, if the period is 100 mS, a 10% on duty cycle would turn the lamp driver 104 on for about 10 mS and off for about 90 mS in every 100 mS period. In another example, if the period is 100 mS, a 1% on duty cycle would turn the lamp driver 104 on for about 1 mS and off for about 99 mS in every 100 mS period.

The filter 112 and analog-to-digital converter 116 may be considered to be a signal conditioning circuit. In an embodiment, some or all of the functions of signal conditioning may be performed in the controller 102. For example, the controller 102 may perform digital filtering of inputs from the analog-to-digital converter 116. The filter 112 and the analog-to-digital converter 116 may be turned on and off by the controller 102. The filter 112 and/or the analog-to-digital converter 1.16 may be turned on and off with less than a 1°/0 on duty cycle by the controller 102, for example by a second control signal 111. In an embodiment, the controller 102 turns the filter 112 and/or the analog-to-digital converter 116 on after the lamp driver 104 and the UV lamp 106 have been turned off. In an embodiment, the filter 112 is left turned on continuously and the analog-to-digital converter 116 is turned on after the lamp driver 104 and the UV lamp 106 have been turned off.

In an embodiment, the analog-to-digital converter 116 is turned on by the controller 102 a predefined time delay after the lamp driver 104 and the UV lamp 106 have been turned off. In an embodiment, the predefined time delay is related to a time constant of the filter 112, for example the predefined time delay is one time constant of the filter 112, two time constants of the filter 112, or some other time duration. As is known to one skilled in the art, the time constant of a filter is the time for a filter to reach a threshold portion of its final output value in response to an input value. In an embodiment the time constant of the filter 112 may be less than 50 mS. In an embodiment, the time constant of the filter 112 may be less than 5 mS. In an embodiment, the time constant of the filter 112 may be less than 1 mS. By turning the analog-to-digital converter 116 on after the lamp driver 104 and the UV lamp 106 are turned off, the noise created by the lamp driver 104 and the UV lamp 106 may be kept out of the signal conditioning circuit and the time constant of the filter 112 can be reduced, thereby producing a more rapid response in the signal conditioning circuit. The electrode 108 outputs a detector electrode signal 110 that is input to the filter 112. The filter 112 outputs a filtered detector electrode signal 114 that is input to the analog-to-digital converter 116. The analog-to-digital converter 116 outputs a digital signal 118 to the controller 102.

Prior art PIDs may leave the UV lamp on continuously. By turning the UV lamp 106 on for a reduced fraction of time—for example for ⅒ the amount of time—the electric power load on a battery 132 that provides power to the PID system 100 may be reduced and a battery life cycle (or recharge cycle) be extended. Additionally, by turning the UV lamp 106 on for a reduced fraction of time, the life of the UV lamp 106 may be extended before it burns out. Further, while the UV lamp 106 is turned on in the presence of VOCs, some polymers may be formed during ionization, and these polymers may deposit and accumulate on the UV lamp 106 and/or on a window of the UV lamp. The deposition of polymers on the UV lamp 106 and/or a window of the UV lamp may degrade the performance of the UV lamp 106.

When the presence of gas is detected by the controller 102 it may output a gas detection alert or signal 120. This signal 120 may cause an indication to be presented by an output device 122 of the PID system 100, for example to a human being associated with the PID system 100. For example, the PID system 100 may be a personal portable photoionization detector carried by a worker in an environment that may expose the worker to VOC hazards. The output device 122 may comprise an aural alert device 124 and/or a visual alert device 126. In an embodiment, the PID system 100 further comprises a microprocessor 128 that receives the signal 120 and provides control signals to the output device 122. The microprocessor 128 may also write records to a memory 130, for example periodic log entries recording levels of gas detection indexed by time. Such log entries may be useful and/or required for auditing safety of work environments, for example.

Figure 5:
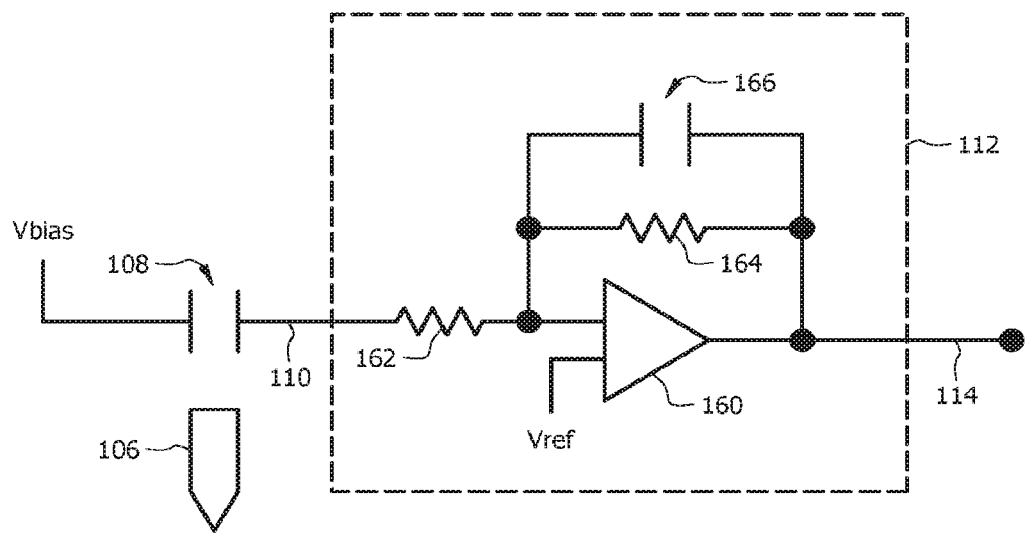
FIG. 5 is an illustration of a portion of a photoionization detector according to an embodiment of the disclosure.

Turning now to FIG. 5, further details of the PID system 100 are described. In an embodiment, the filter 112 may comprise an amplifier 160 that boosts the amplitude of the detector electrode signal 110. In an embodiment, the filter 112 further comprises a first resistor 162, a second resistor 164, and a capacity 166. It is understood that the filter 112 may be implemented in other ways than that illustrated in FIG. 5.

Figure 6:
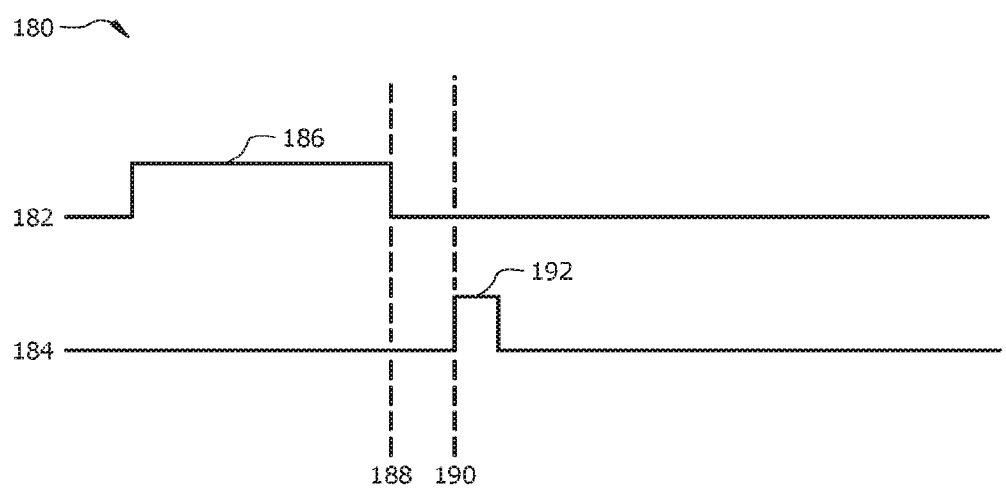
FIG. 6 is an illustration of wave forms according to an embodiment of the disclosure.

Turning now to FIG. 6, a wave form diagram 180 is described. A first wave form 182 represents the first control signal 103 output by the controller 102 for enabling or turning on the lamp driver 104 and hence turning on the UV lamp 106. The first wave form 182 is high at label 186 and enables or turns on the lamp driver 104. A second wave form 184 represents the second control signal 111 output by the controller 102 to enable or turn on the filter 112 and/or the analog-to-digital converter 116. The second wave form 184 is high at label 192 and enables or turns on the filter 112. In an embodiment, the filter 112 is left turned on and the second control signal 111 turns on and off the analog-to-digital converter 116 alone. It is understood that the wave form diagram 180 does not represent the whole duration of a period of the wave forms 182, 184. For example, if the first control signal 103 has a 1% on duty cycle, the portion of the complete wave form period shown in FIG. 6 may only comprise about ⅓₃th of a period. The wave form diagram 180 illustrates the relationship between the time duration of the on interval of the first control signal 103 and the time duration of the on interval of the second control signal 111. The wave form diagram 180 further illustrates the timing sequence of the on interval of the first control signal 103 and the on interval of the second control signal 111.

The on interval of the first control signal 1.03—and hence the on interval of the UV lamp 106—is significantly longer than the on interval of the second control signal 111—and hence the on interval of at least the analog-to-digital converter 116. In an embodiment, the on interval of the first control signal 103 may be at least five times longer than the on interval of the second control signal 111. In an embodiment, the on interval of the first control signal 103 may be at least fifty times longer than the on interval of the second control signal 111. In an embodiment, the on interval of the first control signal 103 may be at least five hundred times longer than the on interval of the second control signal 111. In an embodiment, the first control signal 103 may be on for about 10 mS (milliseconds) while the second control signal 111 may be on for about 100 (microseconds).

The second control signal 111 is turned on after the first control signal 103 is turned off. In an embodiment, there is a time interval between the first control signal 103 being turned off and the second control signal 111 being turned on. For example, the first control signal 103 may be turned off at time 188 and the second control signal 111 may be turned on at time 190. The difference between the time 188 and time 190 may be a predefined time interval related to the constant of the filter 112, for example about one time constant of the filter 112, about two time constants of the filter 112, about three time constants of the filter 112, or some other number. Delaying turning on the second control signal 111 some predefined period of time after turning off the first control signal 103 may result in excluding noise associated with the UV lamp 106 being turned on from the sampling and/or capture of the output of the detector electrode signal 110 and may result in the filter 112 reaching a steady state or a settled value of the output of the detector electrode signal 110. It is noted that it is undesirable to extend the predefined period of time (between time 188 and time 190) excessively, because over time the ionized gases deionize. Thus, the predefined period of time should be long enough to allow the filter 112 to settle after the turning off of the first control signal 103 and hence turning off of the UV lamp 106 and elimination of the electric noise it produces while at the same time short enough to avoid excessive deionization of gases ionized while the UV lamp 106 was turned on. In combination with the present disclosure, one skilled in the art will readily determine a suitable time interval for the offset between time 188 and time 190. As an example, a time interval of about three times the time constant of the filter 112 may be suitable in some embodiments. An another example, a time interval of about 1.5 times the time constant of the filter 112 may be suitable in other embodiments.

Figure 7:
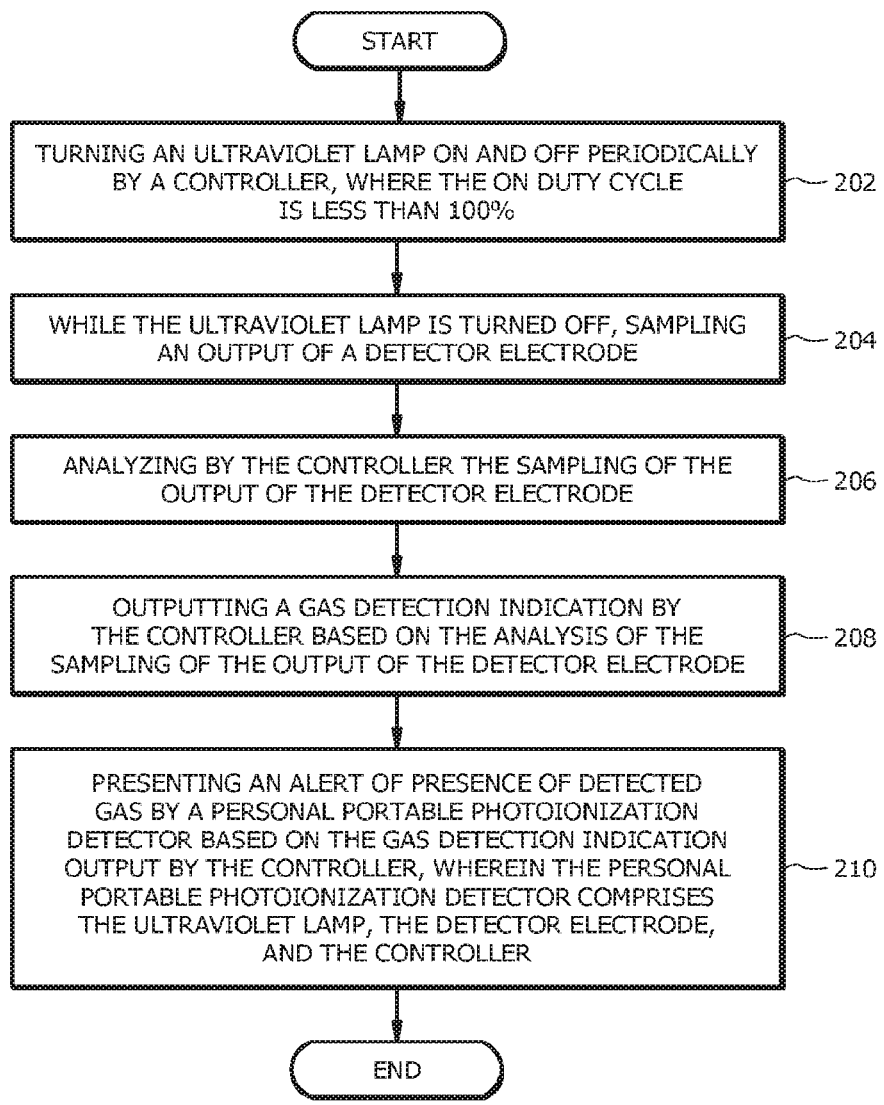
FIG. 7 is a flow chart of a method according to an embodiment of the disclosure.

Turning now to FIG. 7, a method 200 is described. The method 200 may describe a method of using the P1D system 100. In an embodiment, a human being may carry the PID system 100 with him or her into a work environment to warn of the presence of hazardous gases, for example warn of the presence of VOCs. Without limitation, VOCs may comprise various solvents, fuels, degreasers, plastics, heat transfer fluids, lubricants, and others. VOCs may be harmful to human beings if inhaled and/or inhaled in concentrations exceeding a predefined exposure threshold. VOCs may present a risk of explosion or fire, for example when present in concentrations exceeding a predefined threshold. The P1D system 100 may be used to monitor industrial hygiene and safety, environmental contamination and remediation, hazardous materials handling, ammonia detection, and refinery environments. A plurality of PID systems 100 may be used in combination, each tuned to a different kind of gas or VOC based on the primary wavelength of its UV lamp 106.

At block 202, an ultraviolet lamp is turned on and off periodically by a controller, where the on duty cycle is less than 100%. For example, the UV lamp 106 is turned on and off periodically by the controller 102. Said in other words, the UV lamp 106 is turned on and off periodically by the lamp driver 104, and the lamp driver 104 is turned on and off periodically by the controller 1.02. At block 204, while the ultraviolet lamp is turned off, an output of a detector electrode is sampled. The output of the detector (e.g., the detector electrode signal 110) may be sampled after a predefined period of time after the UV lamp 106 is turned off, as described further above with reference to FIG. 3. The sampling of the output of the detector may be performed over a relatively short period of time, for example for about 10 ttS or about 100 μS. The sampling may be performed with an on duty cycle of less than 1%. In an embodiment, the sampling may be performed with an on duty cycle of less than 0.01%.

At block 206, the controller analyzes the sampling of the output of the detector electrode. For example, the controller 102 analyzes the detector electrode signal 110 at least indirectly via the signal conditioning circuit (i.e., filter 112 and analog-to-digital converter 116). At block 208, the controller outputs a gas detection indication based on the analysis of the sampling of the output of the detector electrode. It is understood that the method 200 comprises repeating the processing of blocks 204, 206, 208 on an ongoing basis.

At block 210, optionally (e.g., under the appropriate circumstances, where concentration of gas above a predefined threshold is detected), presenting an alert of presence of detected gas based on the gas detection indication output by the controller. The alert may be presented by the output device 122, for example by the aural alert device 124 and/or the visual alert device 126. In an embodiment, the method 200 may further comprise periodically recording levels of detected gas to the memory 130, for example storing logs to the memory 1.30.

In an embodiment, the PID system 100 may be manufactured by mechanically securing the controller 102, lamp driver 104, UV lamp 106, detector electrode 108, filter 112, analog-to-digital converter 116, output device 122, microprocessor 128, and/or memory 130 to a circuit board and/or package. Suitable electrical lines and connections may be provided between components. The UV lamp 106 may be disposed on the circuit board and/or within the package so as to be proximate to the detector electrode 108 and to radiate UV light towards the detector electrode 108. A fan and air channel may be disposed within the package to direct environmental gases towards the detector electrode 108 and UV lamp 106 when the PID system 100 is in use. The battery 132 may be assembled into the system 100 at a time different from manufacture, for example at time of first use by a human being.

In an embodiment, a photoionization detector is disclosed. The photoionization detector may comprise a detector electrode that outputs a signal, an ultraviolet lamp, a lamp driver communicatively coupled to the ultraviolet lamp and configured to turn the ultraviolet lamp on and off in response to a control input, and a controller that is communicatively coupled to the output signal of the detector electrode and to the control input of the lamp driver, that outputs an indication of gas detection based on the output signal of the detector electrode, and that turns the lamp driver on and off with an on duty cycle of less than 10%. In an embodiment, the controller turns the lamp driver on and off with an on duty cycle of less than 2%. In an embodiment, the photoionization detector further comprises a filter having a time constant of less than 5 milliseconds (mS), where the filter receives the signal output by the detector electrode and outputs a filtered detector electrode signal, wherein the controller is communicatively coupled to the output signal of the detector electrode via the filter and outputs the indication of gas detection based on the filtered detector electrode signal output by the filter. In an embodiment, the photoionization detector further comprises an analog-to-digital converter that outputs a digital filtered detector electrode signal, wherein the controller is communicatively coupled to the filtered detector electrode signal via the analog-to-digital converter and outputs the indication of gas detection based on the digital filtered detector electrode signal output by the analog-to-digital converter, and wherein the controller turns the analog-to-digital converter on and off to achieve an on duty cycle of less than 1% and wherein the controller turns the analog-to-digital converter on when the lamp driver is turned off and turns the analog-to-digital converter off before the lamp driver is next turned on. In an embodiment, the controller turns the analog-to-digital converter on for less than 15 microseconds (μS). In an embodiment, the filter comprises an electronic amplifier.

In an embodiment, a method of detecting presence of gas with a photoionization detector (PID), comprises turning an ultraviolet lamp on and off periodically by a controller, where the on duty cycle is less than 10%; while the ultraviolet lamp is turned off, sampling an output of a detector electrode; analyzing by the controller the sampling of the output of the detector electrode; and outputting a gas detection indication by the controller based on the analysis of the sampling of the output of the detector electrode. In an embodiment, the method further comprises filtering the output of the detector electrode by a filter having a time constant of less than 50 milliseconds (mS), wherein the filtered output of the detector electrode is sampled and provided to the controller for analyzing. In an embodiment, the sampling is enabled by the controller with a duty cycle that is less than 1%. In an embodiment, the sampling comprises analog-to-digital conversion. In an embodiment, the on duty cycle of the ultraviolet lamp is less than 2%.

In an embodiment, a photoionization detector comprises a detector electrode that outputs a signal, an ultraviolet lamp, a lamp driver communicatively coupled to the ultraviolet lamp and configured to turn the ultraviolet lamp on and off in response to a control input, a filter that receives the signal output by the detector electrode and outputs a filtered detector electrode signal, where the filter has a time constant of less than 50 milliseconds (mS), and a controller that is communicatively coupled to the filtered detector signal output by the filter and to the control input of the lamp driver, that outputs an indication of gas detection based on the filtered detector electrode signal output by the filter, and that turns the lamp driver on and off. In an embodiment, the filter has a time constant of less than 5 mS. In an embodiment, the controller turns the lamp driver on and off to achieve an on duty cycle of less than 10%. In an embodiment, the photoionization detector further comprises an analog-to-digital converter that is coupled to the filter and to the controller, that converts the filtered detector electrode signal from the filter to a digital filtered detector electrode signal, and that outputs the digital filtered detector electrode signal to the controller, wherein the controller outputs the indication of gas detection based on the digital filtered detector electrode signal output by the analog-to-digital converter and wherein the controller turns the analog-to-digital converter on and off to achieve an on duty cycle of less than 1% and wherein the controller turns the analog-to-digital converter on when the lamp driver is turned off and turns the analog-to-digital converter off before the lamp driver is next turned on.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method of detecting gas with a photoionization detector system, comprising:
   determining and storing, by a controller, a zero level of a photoionization detector using ambient air inflow, wherein the stored zero level is based on an ambient temperature;
   sensing the ambient temperature;
   adapting the stored zero level algorithmically based on a change sensed in the ambient temperature;
   sampling, by the controller, an output of a detector electrode of the photoionization detector when an ultraviolet lamp is in a turned ON state; and
   comparing the sampled output of the detector electrode to the stored zero level to determine if a threshold concentration of a gas is present.

2. The method of claim 1, further comprising, presenting an alert by the photoionization detector system.

3. The method of claim 2, wherein the controller determines that a threshold concentration of volatile organic compounds (VOCs) is present.

4. The method of claim 1, further comprising, after storing the zero level, turning on and off the ultraviolet lamp by the controller with an on duty cycle of less than 50 percent; and presenting an alert by the photoionization detector system.

5. The method of claim 1, further comprising, after storing the zero level, turning on and off the ultraviolet lamp by the controller with an on duty cycle of less than 10 percent.

6. The method of claim 1, further comprising, after storing the zero level, turning on and off ultraviolet lamp by the controller with an on duty cycle of less than 2 percent.

7. The method of claim 1, further comprising, displaying at least one of a visual and an aural alert when a concentration of the gas exceeds the threshold concentration of the gas.

8. A photoionization detector system, comprising:
   a controller that is communicatively coupled to an output signal of a detector electrode;

a zero calibration application, executed by the controller, configured to:
    turn off an ultraviolet lamp of the photoionization detector system during a zero calibration procedure wherein the zero calibration application is stored in a memory of the photoionization detector system,
    process the output signal of the detector electrode to determine a zero level of the photoionization detector system,
    store the zero level in the photoionization detector system, wherein the stored zero level is based on an ambient temperature, and
    sample and compare the sampled output signal with the stored zero level to determine if a threshold concentration of a gas is present.

9. The photoionization detector system of claim 8, wherein the ultraviolet lamp comprises a vacuum ultraviolet lamp.

10. The photoionization detector system of claim 8, wherein the zero calibration application turns the ultraviolet lamp alternately on and off during the zero calibration procedure.

11. The photoionization detector system of claim 10, wherein the zero calibration application turns the ultraviolet lamp on and off with an on duty cycle of less than 50%.

12. The photoionization detector system of claim 10, wherein the zero calibration application turns the ultraviolet lamp on and off with an on duty cycle of less than 10%.

13. The photoionization detector system of claim 10, wherein the zero calibration application turns the ultraviolet lamp on and off with an on duty cycle of less than 2%.

14. The photoionization detector system of claim 8, wherein the controller determines that a threshold concentration of volatile organic compounds (VOCs) is present.

15. The photoionization detector system of claim 8, further comprise a lamp driver communicatively coupled to the ultraviolet lamp.

16. The photoionization detector system of claim 15, wherein the lamp driver configured to turn the ultraviolet lamp on and off.

17. The photoionization detector system of claim 8, wherein the system senses ambient temperature and algorithmically adapts the stored zero level based on changes in the sensed ambient temperature.

\* \* \* \* \*